(12) United States Patent
Koshti et al.

(10) Patent No.: US 10,654,032 B2
(45) Date of Patent: May 19, 2020

(54) RECYCLABLE CATALYSTS FOR CHLORINATION OF ORGANIC ACIDS AND ALCOHOLS

(71) Applicant: GALAXY SURFACTANTS LTD., Navi Mumbai OT (IN)

(72) Inventors: Nirmal Koshti, Piscataway, NJ (US); Bhagyesh Jagannath Sawant, Kaylan (IN); Arpit Wankhade, Amravati (IN); Pritesh Mhatre, Raigad (IN)

(73) Assignee: GALAXY SURFACTANTS LTD., Navi Mumbai (IN)

( * ) Notice: Subject to any disclaimer, the term of this patent is extended or adjusted under 35 U.S.C. 154(b) by 365 days.

(21) Appl. No.: 15/463,722

(22) Filed: Mar. 20, 2017

(65) Prior Publication Data
US 2017/0274362 A1 Sep. 28, 2017

(30) Foreign Application Priority Data
Mar. 23, 2016 (IN) .............................. 201621010105

(51) Int. Cl.
*B01J 31/06* (2006.01)
*C07C 51/60* (2006.01)
*C08F 8/30* (2006.01)
*C07C 17/16* (2006.01)
*C08F 8/32* (2006.01)

(52) U.S. Cl.
CPC ............... *B01J 31/06* (2013.01); *C07C 17/16* (2013.01); *C07C 51/60* (2013.01); *C08F 8/30* (2013.01); *C08F 8/32* (2013.01); *B01J 2231/40* (2013.01)

(58) Field of Classification Search
CPC .......... B01J 31/06; C07C 17/16; C07C 51/60; C08F 8/32; C08F 8/30
See application file for complete search history.

(56) References Cited

U.S. PATENT DOCUMENTS

| 5,416,193 A | * | 5/1995 | Desai | .................... C07C 231/02 530/333 |
| 6,306,959 B1 | * | 10/2001 | Bolton | .................. B01J 20/265 506/32 |

* cited by examiner

*Primary Examiner* — Peter D. Mulcahy
(74) *Attorney, Agent, or Firm* — Kramer Amado, P.C.

(57) ABSTRACT

The present invention discloses recyclable polymeric catalyst of Formula I, for chlorination of organic acids and alcohols using chlorinating agents such as carbonyl chloride, oxalyl chloride or thionyl chloride,

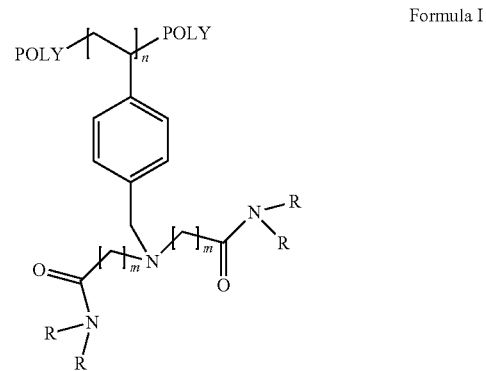

Formula I wherein, 'm' on the pendent groups on polystyrene backbone can have values from 1 to 5 and R is the alkyl group ranging from C1 to C5.

8 Claims, No Drawings

RECYCLABLE CATALYSTS FOR CHLORINATION OF ORGANIC ACIDS AND ALCOHOLS

FIELD OF INVENTION

The invention relates to polymer based catalyst for chlorination. More particularly the invention relates to chlorination of organic acids and alcohols using polymeric catalyst.

BACKGROUND OF INVENTION

Acid Chlorides

Acid chlorides are important intermediates for a variety of bulk chemicals ranging from drug molecules to surfactants for personal cleansing.

Acid chlorides are synthesized by reacting the organic acids with chlorinating agents such as thionyl chloride ($SOCl_2$), phosgene ($COCl_2$), phosphorus trichloride ($PCl_3$), phosphorus pentachloride ($PCl_5$) or oxalyl chloride ($COCl)_2$. This reaction is preferably carried out in the presence of a catalyst, typically N, N-di-substituted formamides and acetamides. The catalysis by formamide type of catalyst goes via Vilsmeier salt (complex) as depicted below:

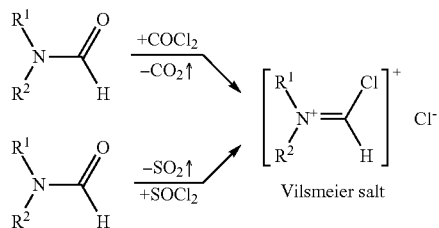

Very commonly, the acid chloride product is purified by distillation. One such method is disclosed in U.S. Pat. No. 4,204,916 (Stauffer Chemical Co., 1980) in which the acid chloride is distilled at sub-atmospheric pressure in the presence of a distillation improvement additive which is a mineral oil or an organopolysiloxane. However, such distillation processes are not only energy-intensive and time-consuming, but they also end up generating undistilled residues that need to be disposed off. This loss of product in distillation process is inevitable. Decomposition of dissolved catalyst complex (Vilsmeier salt) during distillation generates undesired impurities. Also, not all organic acid chlorides are amenable to distillation step for purification.

There are several reports in literature where the product, the acid chloride, is isolated from the catalyst complex by phase separation (product as one phase and the Vilsmeier complex as the other phase). This technique for isolation of the product from the catalyst is applicable to the organic acid chlorides which are liquids and hence can phase-separate from the dark colored Vilsmeier complex. The clean separation of phases is not possible and one can refer to various attempts made in the literature to improve the separation process (U.S. Pat. No. 5,166,427 (1992), U.S. Pat. No. 5,200,560 (1993), U.S. Pat. No. 5,247,105 (1993), U.S. Pat. No. 6,770,783 (2004), U.S. Pat. No. 6,727,384 (2004))

U.S. Pat. No. 5,166,427 provides a process for preparation of an acyl chloride by reacting equimolar amounts of carboxylic acid and phosgene at a temperature between 0-200° C., in the presence of a catalyst adduct of phosgene and N, N-dialkyl formamide (in an amount of 5-200 mol %, based on the carboxylic acid), so as to form two phases, an upper product phase and a lower catalyst adduct phase which can be recycled.

U.S. Pat. No. 5,200,560 teaches a process for preparation of carboxylic acid chloride by reacting carboxylic acid with liquid or gaseous phosgene in the presence of a catalyst adduct of phosgene and N, N-disubstituted formamide. The amount of 'phosgene Vilsmeier complex' is kept between 20-70% molar, based on the formamide.

U.S. Pat. No. 5,247,105 provides a process for preparing a fatty acid chloride. The process comprises allowing phase separation to provide an upper organic layer containing the fatty acid halide and a lower layer of the Vilsmeier complex. The phase separation is effected by carrying out the reaction in the presence of 0.02-0.5 wt % of a fatty acid nitrogen derivative such as fatty nitriles, primary, secondary or tertiary amines, diamines, quaternary ammonium salts, fatty amine oxides, and mono or di-substituted fatty amides.

U.S. Pat. No. 6,727,384 discloses a method for purifying carbonyl chlorides, obtained by a reaction between carboxylic acids and phosgene/thionyl chloride, by treating the reaction product with a hydrohalide of carboxamide such as N, N-dimethyl formamide hydrochloride at a temperature of between −15 to 80° C. The acid chlorides are then phase separated from the catalyst complex. There is an improvement in the color of the acid chloride compared to the original crude, however, the hydrohalide (HCl) content increase which is subsequently driven off by purging nitrogen, to get the desired quality of organic carbonyl chloride.

U.S. Pat. No. 6,770,783 teaches a method comprising introducing gaseous hydrogen chloride during or after the reaction of carboxylic acids with phosgene or thionyl chloride in the presence of a catalyst adduct of an N, N-disubstituted formamide to aid the physical separation of Vilsmeier salt and the acid chloride product.

A recent US Patent Application No. 2010/0099911 provides a method for producing a carboxylic acid chloride which involves decomposing the Vilsmeier complex. The method comprises adding 1.0-3.0 equivalents of the starting carboxylic acid, based on the amount of the catalyst, to the reaction product of a reaction between carboxylic acid and a chlorinating agent, to decompose the Vilsmeier reagent type compounds which remain in the reaction product.

It is very clear that the phase separation of catalyst complex is not a straight forward method and a variety of approaches are reported to make it more effective. The phase separation is not clean and some amount of catalyst complex remains dissolved in the product and that is why the efforts for the progressive improvement are reported in the above mentioned patent-literature. Some of the recent patents indicate that the catalyst amount employed are usually large and additional steps are reported for improving the phase separation like passing hydrogen chloride gas into the reaction mixture (U.S. Pat. No. 6,770,783) or introducing carboxamide hydrohalide (U.S. Pat. No. 6,727,384) or decomposing the catalyst complex by adding acid (US Patent Application No. 2010/0099911).

Recently, Koshti et al. reported a lipophilic carboxamide (U.S. Pat. No. 9,187,407) catalyst for chlorination of fatty acid to affect the homogeneous catalysis. This catalyst decomposes to give the surfactants in the subsequent step involving reaction with amino acids under Schotten Baumann conditions. However, this methodology is useful for making fatty acid chlorides that would be used up subsequently for the synthesis of N-acyl amino acid surfactants (sodium cocoyl glycinate, sodium cocoyl glutamate, sodium lauroyl sarcosinate or sodium cocoyl taurate etc.) because the residual catalyst gets converted into amino acid based surfactants in subsequent stage. In this process the proposed catalyst is not removed from the fatty acid chloride. It gets converted into surfactants during the second Schotten-Baumann step wherein fatty acid chlorides are reacted with amino acids in the presence of a base. So this is a special case of fatty acid chloride synthesis catalyzed by surfactants and not a universal procedure that can be adopted for a variety of acid chlorides that are aromatic (benzoyl chloride) or small chain aliphatic (pivaloyl chloride, valeryl chloride) or p-methoxy cinnamoyl chloride.

Alkyl Chlorides

Alkyl halides are key intermediate in organic synthesis. These are industrial bulk chemicals involved in the manufacture of variety of products that include drugs, dyes, surfactants and a host of fine chemicals. In terms of synthetic transformations, alkyl halides enable bond formation between carbon and oxygen, carbon and nitrogen and carbon and phosphorous. Using transition metal catalysis and organometallic reagents it is possible to form bond between sp3 hybridized carbons (reactions involving Grignard Reagent RMgX and other organic substrates such as carbonyl compounds, Grignard reagent in transition metal catalyzed reactions such as Kulinkovich cyclopropanation, Kumada reaction, other organometallic reagent from alkyl halide such as RZnCl (Negishi reaction)). Alkyl halides can be converted into nitriles, thiols, alkenes, alkynes and ethers etc.

Commercially, alkyl halides are manufactured by halogenations of alkanes and halogenation of alcohols. On large scale, alcohols of different chain lengths are available from petrochemical origin or vegetable origin. Alcohols are usually converted into the corresponding chlorides by gaseous hydrochloric acid, phosphorous trichloride, phosphorous pentachloride, phosphorous oxy chloride, phosgene and thionyl chloride. Alcohols are generally reacted with hydrochloric acid using catalysts like zinc chloride, generating water as by-product. When alcohols are reacted with halogenating agents like thionyl chloride or phosphorous trichloride then the by-products are sulphur dioxide and phosphorous acid respectively, in addition to common by-product of hydrochloric acid.

U.S. Pat. No. 2,331,681 describes the chlorination of glycolonitrile to chloroacetonitrile with thionyl chloride in the presence of the organic bases like pyridine and other tertiary amines such as dimethyl aniline or quinoline. The drawback of the process is the usage of equimolar amounts of catalyst that needs to be separated from the product, alkyl halide.

EP0645357 (1995) teaches a process for preparing alkyl chlorides from corresponding alcohols and stoichiometric amount of catalyst adduct (Vilsmeier salt). The catalyst adduct is formed from N, N-dimethyl formamide with thionyl chloride or phosgene. The disadvantage of this process is the use of equimolar amounts of catalyst.

GB2182039 (1985) discloses the chlorination of alcohols with thionyl chloride or phosgene in the presence of triphenylphosphine oxide or triphenylphosphine sulphide. Again, the amount of catalyst employed is near to stoichiometry.

DE4116365 (1991) teaches the preparation of alkyl, alkenyl and alkynyl chlorides by reacting the corresponding alcohols with phosgene or thionyl chloride in the presence of an aliphatic, cycloaliphatic or cyclic/aliphatic phosphine oxide as catalysts. However, these are very expensive and not readily available catalysts compared to triphenyl phoshine oxide.

U.S. Pat. No. 5,723,704 (1998) reports a two stage process for preparation of the alkyl chloride comprising reacting alcohol with gaseous hydrochloric acid at elevated temperature of 80 to 170° C. and under pressure, to achieve 60 to 90% conversion and then converting unreacted alcohol with phosgene in the presence of a catalyst. The catalyst is selected from guanidine and pyridine derivatives, quaternary ammonium halides and quaternary phosphonium halides.

US 2008228016 (2005) teaches real catalytic quantity of triphenylphosphine oxide catalyst (0.0001 to 0.5 mole equivalent of corresponding alcohol) and thionyl chloride. It uses higher temperature and pressure (0.01 to 10 mPa abs.) for the catalytic chlorination.

U.S. Pat. No. 6,245,954 (2001) teaches alkyl halide from alcohol using phosgene or thionyl chloride under catalysis by urea derivatives. The patent teaches reaction at temperatures of 120-130° C. This process is an example of homogeneous catalysis with substituted urea derivatives as catalyst. After the reaction, the insoluble impurities can be filtered off. However, for soluble impurities subsequent purification steps like distillation are needed. The same process limitation is reported with catalysts like triphenyl phosphine or phosphonium sulphide (GB182039) and other aliphatic phosphorous compounds (EP514683) which are difficult to remove and the residue after distillation containing phosphorous compounds are difficult to dispose off.

Hydrochloric acid is also a preferred industrial chlorinating agent. A number of processes are reported by patented literature using HCl and aqueous alkyl pyridine hydrochloride solutions as catalysts (EP0789013, DE10158376 and DE10247497). Alkyl halides made by these processes are purified by very complex procedure involving extraction, filtration though silica gel and subsequent distillation.

JPS53015303 describes the preparation of alkyl halides by reacting alcohols with an aqueous solution of hydrogen halide in the presence of quaternary ammonium compounds as a catalyst. Primary alcohols are chlorinated with aqueous hydrochloric acid in micellar medium (Synthesis 11, 868-871 (1988)) in the presence of quaternary ammonium surfactants. The isolation of quaternary ammonium compound is necessary for obtaining clean product.

U.S. Pat. No. 7,652,180 (2010) reports an improved procedure using gaseous HCl and substituted N-pyridinium chloride or N-substituted and C-substituted imidazolidium chlorides as catalysts. Reaction is carried out at a temperature of 60-160° C. The biphasic reaction product is separated; organic phase is worked up and is finally distilled to give alkyl halide.

Formamide or carboxamide type of catalysts or tertiary amines or any other soluble catalysts (homogeneous catalysis) that are used for chlorination of alcohols have same difficulty of isolation of product from the catalyst-product mix that results at the completion of reaction.

Thus, there is a need in the art for an improved process wherein the catalyst can be cleanly isolated from the products (acid chlorides or alkyl chlorides) and can be recycled a number of times without losing its catalytic efficiency. The clean and quantitative isolation of the catalyst would avoid subsequent steps of purification like distillation or crystallization and the waste generated. Because, these additional purification steps result in significant loss of yield, higher energy consumption and longer batch cycle time resulting into lower productivity.

OBJECT OF THE INVENTION

It is an object of the present invention to overcome the drawbacks of the prior art of synthesis of organic acid chlorides and alkyl chlorides, such as 1) ease of separation of products from the catalyst 2) recycling of catalyst several times without losing the efficiency 3) avoiding purification steps and thereby reducing the batch cycle time, reducing the energy consumption, preventing loss of yield and avoiding waste generation and cost of waste disposal.

It is an objective of the present invention to provide a universal catalyst for chlorination of organic acids and alcohols.

It is another objective of the present invention to provide a universal process for the manufacture of all types of organic acid chlorides including short chain aliphatic acid chlorides, long chain aliphatic acid chlorides and aromatic acid chlorides.

Yet another objective is to provide a process for the manufacture of alkyl chlorides.

SUMMARY OF INVENTION

The present invention discloses recyclable polymeric catalyst of Formula I for chlorination of organic acids and alcohols using reagents like thionyl chloride, carbonyl chloride or oxalyl chloride, wherein, R is selected from C1 to C5 alkyl groups and 'm' can have values from 1 to 5.

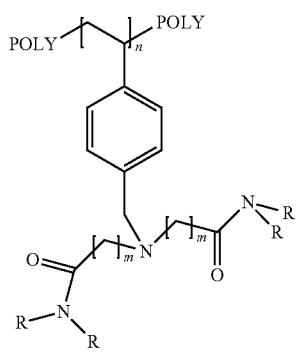

Formula I

According to another aspect of the present invention there is provided a process for the synthesis of polymeric catalyst by functional group modification of chloromethyl polystyrene or aminomethyl polystyrene. The polymeric catalyst exhibits remarkable efficiency though heterogeneous catalysts in general are slightly less efficient in terms of turnover number than the homogeneous catalysts. The isolation of the heterogeneous catalyst from the product is extremely facile. The heterogeneous catalyst of the present invention can be recycled several times with no loss of catalytic efficiency. The yield and conversions of chlorination are quantitative. Thus, the overall chlorination process is 'green' (significantly reduced batch time, low energy consumption) without any wastage and effluent generation (no residue after distillation/fractionation) and extremely cost-effective (low energy consumption) and efficient.

Moreover, the process described in the present application avoids use of monomeric, toxic catalysts like DMF (N, N-dimethyl formamide) and the possibility of contaminating products despite the best separation techniques.

In an another embodiment the present invention relates to the use of polymeric catalyst of Formula I to synthesize a variety of short chain and long chain acid chlorides, aromatic acid chlorides and alkyl chlorides.

DETAILED DESCRIPTION OF INVENTION

In accordance with the above objectives, the present invention provides a recyclable catalyst of Formula I for chlorination of organic acids and alcohols using carbonyl chloride, oxalyl chloride or thionyl chloride. It is the heterogeneous nature of the catalyst that offers the convenience of isolating the product, an organic acid chloride/alkyl chloride, from the catalyst obviating all the conventional steps of purification. The yields and catalytic efficiency remains unaffected even after several cycles.

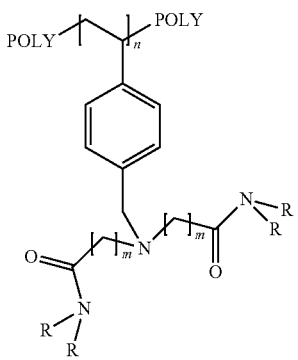

Formula I wherein, R is selected from C1 to C5 alkyl groups; 'm' can have values from 1 to 5; and 'Poly' refers to polystyrene backbone.

The polystyrene backbone of the polymer catalyst of Formula I is derived from either chloromethyl polystyrene or aminomethyl polystyrene in resin form.

According to the invention, a process for preparation of the polymer catalyst of Formula I which comprises;

reacting acrylates or iminodiesters with polystyrene backbone to obtain amino diester unit tethered to polystyrene backbone; and subjecting the amino diester unit tethered to polystyrene backbone to aminolysis with an amine to obtain the catalyst of formula I.

The amine may be selected from secondary amine or cyclic secondary amine. Thus the polymer catalyst of Formula I is based on the functionalization of polystyrene backbone as shown in Scheme 1, wherein, commercially available chloromethyl polystyrene of Formula II is reacted with imino alkyl ester (iminodiesters), SN2 displacement of benzylic chloride by nitrogen nucleophile to give compounds of Formula III. This reaction is effected with or without solvent using excess of imino alkyl esters.

The degree of chloromethylation on the polystyrene backbone is given by the suppliers of Merrifield type of resins. It is defined in terms of mmols of chlorine per gram of the polymer. Merrifield resins are copolymers of styrene and chloromethyl styrene and a range of chloromethyl labeling is available. Merrifield resins are cross-linked with cross linking agents like divinyl benzene. A variety of such resins are available with well-defined particle size ranging from 20 mesh to 500 mesh and chloromethyl label ranging from 0.5 mmol/g to 5 mmol/g of resin. Non-cross-linked chloromethyl in polystyrene in powder form can be used for the chemistry depicted in Scheme 1. However, cross-linked polystyrenes in the resin form are easy to work with, on an industrial scale for heterogeneous catalysis. It is possible to use chloromethyl or aminomethyl polystyrene with less or no cross linking, as long as the particles are not too fine to be filtered by normal methods of filtration. The basic requirement for the resin or any other particulate form is the ease of quantitative filtration. It is important that the polymeric support is completely insoluble in ethereal solvents like diethyl ether or tetrahydrofuran and chlorinated solvents like dichloromethane. For the present work Merrifield resin with 50-100 mesh (2.5-4.0 mmol/g chlorine loading 1% cross-linked with divinyl benzene) is used. Also, some acid chlorides have been chlorinated by dissolving them in dichloromethane and then reacted with chlorinating agent under the catalysis of compound of Formula I.

Examples 1 to 11 describe the synthesis of polymeric catalysts of Formula I of the present invention in detail. In Scheme 1 (Examples 1 and 2), diethyl imino diacetate is reacted with chloromethyl polystyrene to give aminodiacetate (Formula III) tethered to polystyrene backbone, which is subsequently subjected to aminolysis with secondary amine such as diethyl amine. The secondary amines can be with same alkyl groups as in dimethyl, diethyl, dipropyl or dibutyl or with mixed alkyl groups as in methyl ethyl amine or ethyl butyl amine or any other combination. Cyclic secondary amines like piperidine, morpholine or pyrrolidine can also be selected for aminolysis of compound of Formula III. Typically, elemental nitrogen content of compound of Formula III ranges from 2.5 to 3.5%. On reacting compounds of Formula III with small chain dialkyl amines, the nitrogen content increases to 4 to 6% in compounds of Formula I. The Infra-Red (IR) spectrum shows ester carbonyl stretch in the compounds of Formula III at 1730 to 1735 cm-1 and carbonyl of amide stretch in compound of Formula I at 1650 to 1670 cm-1.

The stoichiometry of chloromethyl polystyrene to dialkyl imino dipropionate or diacetate is 1:1 to 1:4, more preferable is 1:2 to 1:3. The exact chloride content of the chloromethyl polystyrene is determined by reacting it with tertiary amines and the liberated chloride ion is then titrated with silver nitrate (Hawk, P. B.; Oser, B. L.; Summerson, W. H. "Practical Physiological Chemistry" Blakiston, 13. edition, 1954, p. 955). Determination of benzylic chloride content of Merrifield resin helps in deciding the stoichiometry for the reaction between the chlorinated resin and the nitrogen nucleophile like diethyl iminodiacetate. The same analytical method is used to find out the unreacted benzylic chloride of chloromethyl styrene in polymers of Formulae III and IV. Typical reaction conditions are given in Example 1. For the second step of aminolysis of compound of Formula III, large excess of short chain dialkyl amines are used. The excess secondary amines are recovered and recycled. Upon completion of reaction, the polymeric resin beads of Formula I are filtered off and washed thoroughly with solvents as described in Example 2.

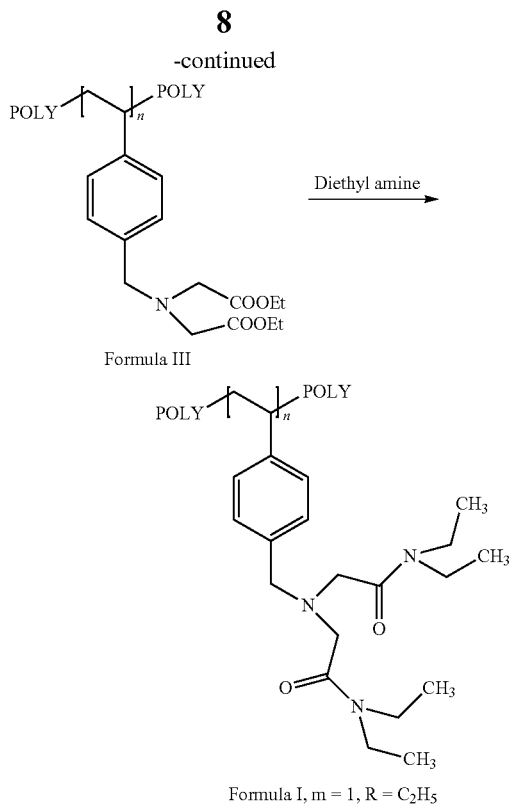

Examples 3, 4, 5 and 6 cover Scheme 2 for the synthesis of polymeric catalyst of Formula I. Analogous to Scheme 1; Scheme 2 depicts reaction of diethyl imino dipropionate with chloromethyl polystyrene to afford the corresponding diethyl ester of Formula IV. The loading of amino ester moiety seems quantitative as judged by the elemental analysis of functionalized polystyrene that showed negligible chlorine content and 2.9% of nitrogen content. Aminolysis of functionalized polystyrene of Formula IV with diethyl amine gives the polymeric compound of Formula I (m=2). Diethyl iminodipropionate of Scheme 2 is prepared by the literature based procedure (M. Srujan, Biomaterials, 32, pp 5231-5240, 2011) by debenzylation (hydrogenolysis) of the Michael adduct derived from benzyl amine and ethyl acrylate. Other lower alkyl acrylate esters can be used for creating the Michael adduct of benzyl amine. Debenzylation is best affected by palladium (5% on charcoal) in the presence of either molecular hydrogen or by transfer hydrogenation.

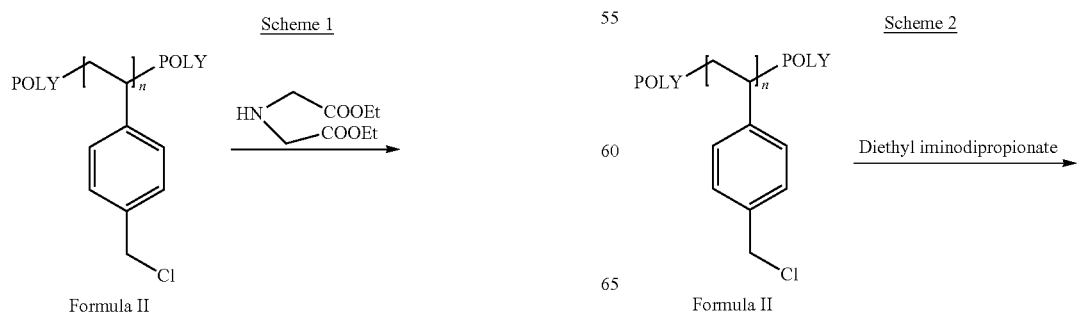

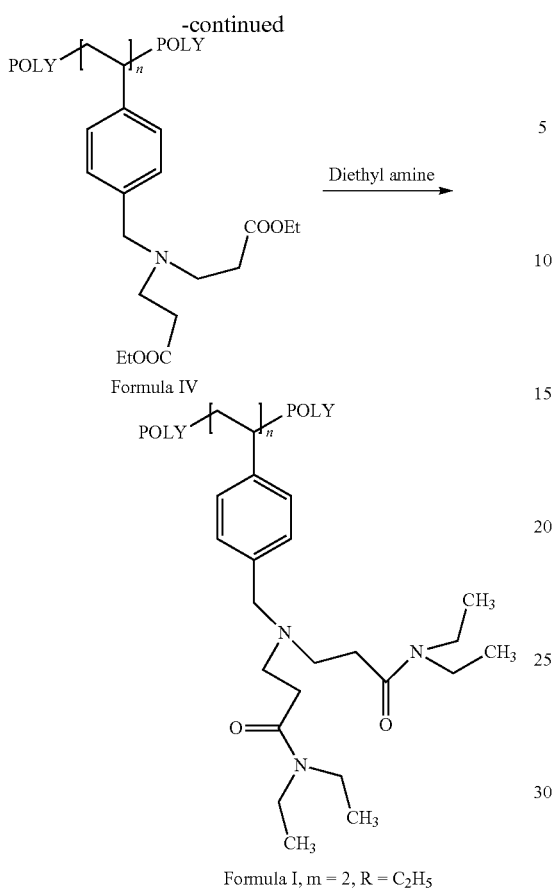

Formula IV

Formula I, m = 2, R = C₂H₅

Synthesis of polymers of Formula I analogous to Scheme 2 is described in Example Nos. 7a, 7b, 8 and 9, wherein benzyl amine is quantitatively reacted with methyl acrylate at room temperature to form the Michael adduct. The diadduct is then debenzylated or hydrogenolyzed with palladium on charcoal to afford dimethyl imino dipropionate (CAS no. 3518-82-2) in quantitative yield. The debenzylation can be affected with palladium and cyclohexene or other hydrogen donors in a typical transfer-hydrogenation procedure. Chloromethyl polystyrene is then reacted with dimethyl iminodipropionate (Example 8) to give ester functionalized polystyrene. This is then converted to polyamide resin of Formula I by reacting with diethylamine (Example 9). Diethyl iminodipropionate (CAS no. 3518-88-5) or dimethyl iminodiacetate can react further with polymers of Formula III and Formula IV and this kind of functionalization is not ruled out. This kind of dendrimeric functionality can generate more catalytic sites on the polystyrene backbone.

Polystyrene resin of Example 9 has been extensively used in catalyzing the chlorination of host of organic acids and alcohols as described in Experimental section.

The second approach of synthesizing functionalized polystyrenes of Formula I is given in Scheme 3 (Examples 10 and 11). Michael adduct of commercially available aminomethyl polystyrene (Formula V) with methyl acrylate gives amino diester unit tethered to polystyrene backbone (Scheme 3, Formula VI). Subsequent aminolysis of polymer of Formula VI with a secondary amine gives the compound of Formula I. The aminomethyl polystyrene (Formula V) used for this synthesis has mesh size of 200 to 400 (2% crosslinked with divinyl benzene) with about 2 mmol of amino functionality's loading per gram.

Scheme 3

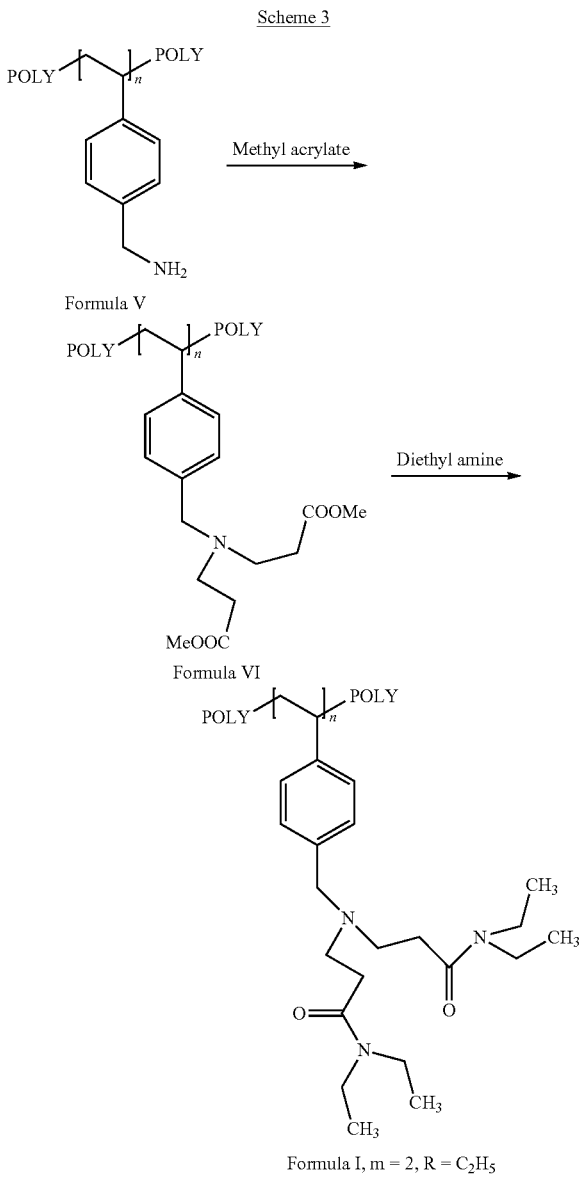

Formula V

Formula VI

Formula I, m = 2, R = C₂H₅

It is obvious to the person skilled in the art that the monomeric units with imino acetate/propionate groups attached (Formula VII) can be homopolymerized or copolymerized with another monomer or with another crossed linking agent to create polymeric catalyst with pendent ester groups (alkyl acetates or alkyl propionates) that can be reacted with short chain dialkyl amines to get formamido or carboxamido groups. Alternatively, the amide linkage can be created on the monomer and that can be homopolymerized or copolymerized to get the polymer with pendent amido functionality. In the present invention commercially available Merrifield resins have been used that have polystyrene backbone. However, any other polymer such as polyacrylate or polymethacrylate type can be exploited for tether amido functionality. For example, secondary amine can be reacted with resinous acrylate to create the amide linkage for the catalytic sites. For a longer tether, imino di t-butyl butyrate or propionate can be reacted with polyacrylate resin and then the t-butyl esters can be subjected to aminolysis with short chain secondary amines.

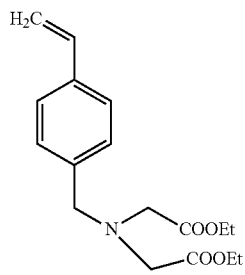

Formula VII

In a similar manner, a preformed catalytic unit (as shown in Scheme 4 below) can be synthesized and tethered to chloromethyl polystyrene to afford the polymeric catalyst of Formula I. In summary, the methodology described in this patent application can be exploited to create heterogeneous polymeric catalysts.

Scheme 4

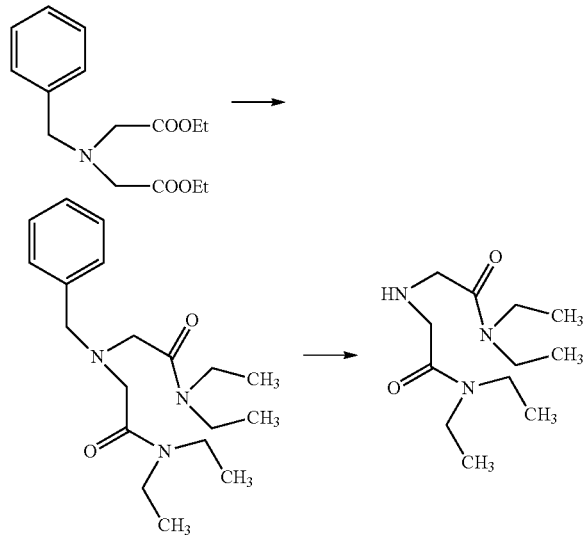

According to the present invention, the process described is very cost-effective since it avoids purification steps that result in significant reduction in energy consumption. The process of the present invention also avoids laborious steps of purification and loss of product that entails the purification steps.

The Catalysis: Chlorination of Organic Acids and Alcohols

Polymeric catalyst of Formula I is used to catalyze the chlorination of several organic acids and alcohols (Table 1).

TABLE 1

| Sr. No. | Organic Acid/Alcohol | Example No. | Reagent | Polymeric Catalyst |
|---|---|---|---|---|
| 1 | Coco fatty acid | 12 | $SOCl_2$ | Ex 9 |
| 2 | Coco fatty acid | 17 | $SOCl_2$ | Ex 11 |
| 3 | Lauric acid | 13 | $(COCl)_2$ | Ex 9 |
| 4 | Benzoic acid | 14 | $SOCl_2$ | Ex 9 |

TABLE 1-continued

| Sr. No. | Organic Acid/Alcohol | Example No. | Reagent | Polymeric Catalyst |
|---|---|---|---|---|
| 5 | Methoxy acetic acid | 16 | $SOCl_2$ | Ex 9 |
| 6 | Pivalic acid | 18 | $(COCl)_2$ | Ex 9 |
| 7 | Undecylenic acid | 21 | $(COCl)_2$ | Ex 9 |
| 8 | p-methoxy cinnamic acid | 15 | $SOCl_2$ | Ex 9 |
| 9 | n-Octanol | 19 | $SOCl_2$ | Ex 9 |
| 10 | Behenyl alcohol | 20 | $SOCl_2$ | Ex 9 |

Cocofatty acid is converted to cocoyl chloride which is industrially used to manufacture several surfactants such as sodium cocoyl glycinate, sodium cocoyl taurate, sodium cocoyl glutamate and sodium cocoyl sarcosinate. Cocofatty acid is typically derived from coconut oil or palm kernel oil. It is a mixture of even number fatty acids with carbon number varying from C8 to C18. Cocofatty acid used in Example 12 has alkyl chain distribution ranging from $C_8$ to $C_{16}$ and the details of the composition are given. The polymeric catalyst of Example 9 is used to demonstrate the catalysis and its recyclability. In Example 12, under unoptimized conditions, on a 200 mmol scale, polymeric catalyst employed is about 2% by weight of the organic acid substrate. The polymer catalyzed chlorination of fatty acid with thionyl chloride is completed within three hours as indicated by the weight percentage of unconverted fatty acid in the cocoyl chloride product. On the similar molar scale, the 'non-catalyzed' reaction of coco fatty acid with thionyl chloride does not go to completion even after 8 hours. Typically, after eight hours, around 10% by weight of unconverted fatty acid is found in the final product and progresses very slowly and practically remains constant as found by the gas chromatographic analysis after 12 hours and 16 hours. Table of Example 12 shows that after three hours in a catalyzed chlorination, the unconverted fatty acid is less than 1% whereas under exactly identical reaction conditions in a non-catalyzed reaction the unconverted fatty acid after three hours is about 40% of the original quantity. Example 12 shows analysis of six cycles of catalysis wherein rate of sixth cycle is exactly the same as the first cycle indicating no deterioration of catalytic efficiency. After every cycle the catalyst is simply filtered off and is used immediately for the next cycle. The quality of the product produced from half a dozen cycles is exactly identical, not just in terms of chemical properties but also in terms of physical properties like color and odor. For converting fatty acid to fatty acid chloride, the same catalyst has been recycled for twelve successful cycles. Example 13 demonstrates use of oxalyl chloride to convert lauric acid into lauroyl chloride that is catalyzed by the polymeric catalyst of Example 9. Preparation of simple, short chain aliphatic acid chloride and a branched aliphatic acid chloride have been exemplified by methoxy acetyl chloride and pivaloyl chloride (Examples 16 and 18). In Example 17, the coco fatty acid is converted to corresponding cocoyl chloride using thionyl chloride. This chlorination is catalyzed by polymer of Example 11 (Scheme 3) and recycled successfully for two additional cycles of the same scale. Another fatty acid with unsaturation, undecylenic acid, is converted into its acid chloride by oxalyl chloride in Example 21. Synthesis of aromatic acid chloride like benzoyl chloride is presented in Example 14. Example 15 demonstrates clean synthesis of p-methoxy cinnamoyl chloride from corresponding acid in solvent like dichloromethane. Example 14 demonstrates successful catalysis of chlorination of aromatic acid derivatives in a solvent wherein, example 15 explains catalysis of acrylic acid derivative in a solvent. Examples 19 and 20 exemplify the catalysis of medium chain and long chain alcohols into corresponding alkyl halides. Just like chlorination of acids, the significant difference between catalyzed chlorination of alcohols by compound of Formula I and non-catalyzed chlorination of alcohol with thionyl chloride is observed (Example 19). In addition to carboxamide moieties, the tertiary nitrogen sites of the polymers of Formula I can also be the catalytic sites for chlorination of alcohols. The catalysis is studied with chlorination of n-octanol. The chlorination is carried out at 70° C. using stoichiometric quantity of alcohol and thionyl chloride. The compound of Formula I (Example 9) employed for the catalysis was 1% by weight based on n-octanol. After eight hours at 70° C., there are no unconverted n-octanol or sulphate esters of octanol in the product, octyl chloride. In the non-catalyzed reaction run under identical conditions, after 8 hours, the product was predominantly about 85% dioctyl sulphate (undesired compound) and about 15% the desired product, octyl chloride.

The above described features, benefits and advantages of the present disclosures will be appreciated and understood by those skilled in the art from the following detailed experimental and the claims.

The present invention is now described by way of working on limiting illustrative examples. The following examples are given in illustration in details but the invention is not limited to the examples.

The organic acid chlorides are analyzed by potentiometric titration as described in Quantitative analysis via functional groups (C. R Stahl and S. Siggia, Analytical Chemistry, Volume 28, Pg 71-73, 1956). This procedure analyzes both organic acid chloride and unconverted organic acid. Gas chromatography (GC) is used wherever applicable depending upon the ease of volatility of both; the starting material, the organic acid and the end product, organic acid chloride.

In case of alcohols selected, both octanol and behenyl alcohol, the chlorination reaction aliquots are washed with water and dried over sodium sulphate (if necessary a volatile solvent (diethyl ether or methylene dichloride) is used and dried samples are analyzed by capillary gas chromatography using flame ionization detector. Chloromethyl polystyrene (Product no. 577901) as well as aminomethyl polystyrene (Product no. 473669) and diethyl iminodiacetate (Product no. 444049) are purchased from Aldrich chemicals.

Example 1

Functionalization of Merrifield Resin: Reaction of diethyl iminodiacetate with the Resin: N, N-di (ethyl acetate), aminomethyl polystyrene A mixture of chloromethyl polystyrene (2 g, equivalent to 8 mmol of chloromethyl group), dioxane (10 mL) and diethyl iminodiacetate (2.0 g, 10.5 mmol) was stirred under nitrogen at 80-85° C. for 24 hours.

The chloromethyl styrene (Merrifield resin) was filtered and washed with diethyl ether (20 mL). The washed resin was further stirred with ether (20 mL) for 30 minutes and the resin was separated by centrifugation from solvent. This operation of stirring with ether and then centrifugation to separate it from solvent was repeated two times. It was further washed with dichloromethane (20 mL×2). Drying on a rotary evaporator under vacuum yielded (2.6 g) granular resin with diethyl acetate moiety.

IR (cm-1): 1739

Example 2

Synthesis of N, N-di (N, N-diethyl acetamido) aminomethyl polystyrene

Heterogeneous mixture of N, N-di (ethyl acetate), aminomethyl polystyrene resin of Example 1 (2.2 g), dioxane (10 mL) and diethyl amine (10 mL) was stirred at 145-150° C. for 24 hours. The reaction was carried in a pressure vessel at a pressure of 8 kgf/cm2 at 150° C. The resin beads were then separated by filtration and washed with diethyl ether (20 ml×3) and dichloromethane (20 ml×3) several times. Drying under vacuum yielded 2.6 g of N, N-diethyl amido functionalized resin as pale yellow beads.

IR (cm$^{-1}$): 1648, 1659

Example 3

Synthesis of β-Alanine, N-(3-ethoxy-3-oxopropyl)-N-(phenylmethyl)-, ethyl ester (N, N-3-diethyl propionate) N, N-di ethyl propionate benzyl amine To a stirred mixture of ethyl acrylate (100 g, 1000 mmol) in ethanol (300 mL) under nitrogen atmosphere, benzyl amine (30 g, 280 mmol) was added drop wise at room temperature over a period of 30 minutes. The reaction mixture was refluxed at 100-105° C. for 24 hours. The excess of ethyl acrylate was removed under reduced pressure to give β-Alanine, N-(3-ethoxy-3-oxopropyl)-N-(phenylmethyl)-, ethyl ester (74 g, 97%) as pale yellow viscous oil.

IR (cm$^{-1}$): 1730, 2825, 2981.
$^1$H NMR (CDCl$_3$): δ 1.13 (6H, t, J=6 Hz), 2.38 (4H, t, J=6 Hz), 2.69 (4H, t, J=5.4), 3.49 (2H, s), 4.0 (4H, q, J=5.4 Hz), 7.1 to 7.2 (5H, Ar)

Example 4

Synthesis of Diethyl 3, 3'-iminodipropionate

The Michael adduct of benzyl amine and ethyl acrylate of Example 3 (10 g, 32.5 mmol) in ethanol (50 mL) and Pd on charcoal (5% Pd/C, 100 mg) was stirred under hydrogen at atmospheric pressure for 20 hours. The catalyst was filtered off and the filtrate was made free of any volatiles by rotary evaporation under reduced pressure at 50° C. to yield diethyl iminodipropionate (6.6 g, 93.4%) as pale yellow viscous liquid.

IR (cm$^{-1}$): 1728, 2838, 2981 and 3330
$^1$H NMR (CDCl$_3$): δ 1.90 (6H, t, J=5.4 Hz), 2.82 (4H, t, J=6 Hz), 2.43 (4H, t, J=4.8 Hz), 4.0 (4H, q, J=5.4 Hz)

Example 5

Functionalization of Merrifield Resin: Reaction of diethyl imino dipropionate with the Resin: N, N-di (ethyl propionate), aminomethyl polystyrene A mixture of chloromethyl polystyrene (2 g, equivalent to 8 mmol of chloromethyl group), 1, 4-Dioxane (10 mL) and diethyl iminodipropionate of Example 4 (6.0 g, 27.7 mmol) was stirred under nitrogen at 80-85° C. for 24 hours. The Merrifield resin was filtered and washed with diethyl ether (20 ml). The washed resin was further stirred with ether (20 mL) for 30 minutes and resin was separated by centrifugation from solvent. This operation of stirring with ether and then centrifugation to separate it from solvent was repeated two times. It was further washed with dichloromethane (20 mL×2). Drying on rotary evaporator under vacuum yielded (2.4 g) granular resin with diethyl propionate moiety. Nitrogen content of this resin was found to be 2.89%.

IR (cm$^{-1}$): 1727, 2839 and 2980

Elemental analysis (CHN) was found to be as given below:

C: 87.68%, H: 8.7%, N: 2.84%

Example 6

Functionalization of Polystyrene Example 5: Synthesis of N, N-di (N, N-diethyl propionamido) aminomethyl polystyrene Heterogeneous mixture of N, N-di (ethyl propionate), aminomethyl polystyrene resin of Example 5 (2.4 g), 1, 4-Dioxane (10 mL) and diethyl amine (10 mL) was stirred at 145-150° C. for 24 hours. The resin beads were then separated by filtration and washed with diethyl ether (30 mL×3) and dichloromethane (30 mL×3). Drying under vacuum yielded 2.6 g of N, N-diethyl amido functionalized resin as pale yellow beads.

IR (cm-1): 1648

Elemental analysis is found to be as given below.

C: 75.69, %; H: 8.93%, N: 5.27%

Example 7a

Synthesis of N, N-di methyl propionate benzyl amine

To stirred methyl acrylate (112 g, 1302 mmol) and methanol (400 mL) under nitrogen atmosphere, benzyl amine (35 g, 326 mmol) was added drop wise at room temperature over a period of 30 minutes and continued stirring for 24 hours. The excess of methyl acrylate was removed under reduced pressure using a rotary evaporator to give N, N-di methyl propionate benzyl amine (90 g, 99%) as pale yellow viscous oil.

IR (cm$^{-1}$): 1734, 2830, 2952

$^1$H NMR (CDCl$_3$): δ 2.36 (t, 4H, J=5.1 Hz), 2.69 (t, 4H, J=5.4 Hz), 3.4 (s, 2H), 3.53 (s, 6H), 7.1-7.17 (5H, Ar)

Example 7b

Synthesis of dimethyl 3, 3'-iminodipropionate

The Michael adduct of benzyl amine and methyl acrylate (20 g, 71.6 mmol) in methanol (100 mL) and Palladium on charcoal (5% Pd/C, 100 mg) was stirred under hydrogen at atmospheric pressure for 20 hours. The catalyst was filtered off and the filtrate was made free of any volatiles by rotary evaporation under reduced pressure at 50° C. to yield dimethyl iminodipropionate (13 g, 96%) as a pale yellow viscous liquid.

IR (cm$^{-1}$): 1728, 1838, 3330

$^1$H NMR (CDCl$_3$): δ 2.44 (t, 4H, J=4.8 Hz), 2.82 (t, 4H, J=4.8 Hz), 3.62 (s, 6H), 3.53 (s, 6H)

Example 8

Functionalization of Merrifield Resin: Reaction of dimethyl imino dipropionate with the Resin: N, N-di (methyl propionate), aminomethyl polystyrene A mixture of chloromethyl polystyrene (4 g, equivalent to 16 mmol of chloromethyl group), 1, 4-Dioxane (10 mL) and dimethyl iminodipropionate of 7b (8 g, 42.3 mmol) was stirred under nitrogen at 80-85° C. for 24 hours. The Merrifield resin was filtered and washed with diethyl ether (30 mL). The washed resin is further stirred with ether (30 mL) for 30 minutes and the resin was separated by centrifugation from solvent. This operation of stirring with ether and then centrifugation to separate it from solvent was repeated two times. It was further washed with dichloromethane (30 mL×2). Drying on rotary evaporator under vacuum yielded 4.8 g granular resin with diethyl propionate moiety.

IR (cm$^{-1}$): 1736, 2847 and 2980

Elemental analysis (CHN) was found to be as given below:

C: 87.68%; H: 8.71%, N: 2.84%

Example 9

Functionalization Polystyrene of Example 8

Synthesis of N, N-di (N, N-diethyl propinamido) aminomethyl polystyrene

Heterogeneous mixture of N, N-di (methyl propionate), aminomethyl polystyrene resin from Example 8 (4.0 g), 1,4-Dioxane (10 mL) and diethyl amine (10 mL) was stirred at 145-150° C. for 24 hours in a pressure vessel (Pressure: 8 kgf/cm2). The resin beads were then separated by filtration and washed with diethyl ether (30 mL×3) and dichloromethane (30 mL×3). Drying under vacuum yielded 4.8 g of N, N-diethyl amido functionalized resin as pale yellow beads.

IR (cm$^{-1}$): 1651, 2849, 2923 and 3026

Elemental analysis (CHN) was found to be as given below:

C: 81.35%; H: 9.23%; N: 4.87%

Example 10

Synthesis of N, N-di (methyl propionate), aminomethyl polystyrene: Reaction of amiomethyl polystyrene with methyl acrylate A heterogeneous mixture of aminomethyl polystyrene (3.0 g of aminomethyl, mesh size 200 to 400, cross-linked with 2% divinyl benzene, procured from Aldrich), 1,4-Dioxane (10 mL) and methyl acrylate (20 g, 232.6 mmol) was stirred at room temperature for 4 hours and then at 80-85° C. for 8 hours. It was then filtered and washed with diethyl ether (30 mL×3) and dichloromethane (30 mL×3). Drying under reduced pressure yielded 4.45 g of resin.

IR (cm$^{-1}$): 1731, 2849, 2924

Example 11

Synthesis of N, N-di (N, N-diethyl propionamido) aminomethyl polystyrene

Functionalization of N, N-di (methyl propionate), aminomethyl polystyrene

Heterogeneous mixture of N, N-di (methyl propionate), aminomethyl polystyrene resin (3.4 g), 1, 4-dioxane (10 mL) and diethyl amine (10 mL) was stirred at 145-150° C. for 24 hours. The resin beads were then separated by filtration and washed with diethyl ether (30 mL×3) and dichloromethane (30 mL×3). Drying under vacuum yielded 4.2 g of N, N-diethyl amido functionalized resin as pale yellow beads.

IR (cm$^{-1}$): 1670

Example 12

Synthesis of cocoyl chloride from cocofatty acid and thionyl chloride Catalyzed by polymeric Catalyst of Example 9

Commercially available cocofatty acid is a mixture of fatty acids with alkyl chain of C8 to C16 and the alkyl chain distribution is as follows:

C8 6.0%, C10 5.4%, C12 60%, C14 22.2%, C16 6.5%.

To a stirred mixture of cocofatty acid (Average molecular weight of 200, 40 g, 200 mmol) and 0.8 g of resin of Example 9 at room temperature under nitrogen atmosphere, thionyl chloride (25 g, 210 mmol) was added over a period of 30 minutes. The reaction was continued at 30-35° C. and the progress was monitored by estimating the unconverted fatty acid. The reaction was stopped when free fatty acid is less than 1.0% by weight (2 to 3 hours including addition time). The catalyst was filtered and recycled for the next experiment at the same scale.

The results are tabulated below:

| Number of cycles | Time required for 98% conversion (hours) | Unconverted fatty acid (%) | Color on APHA scale |
|---|---|---|---|
| 0 | 3 | 0.77 | <100 |
| 1 | 3 | 0.78 | <100 |
| 2 | 3 | 0.75 | <100 |
| 3 | 3 | 1.0 | <100 |
| 4 | 3 | 0.90 | <100 |
| 5 | 3 | 0.9 | <100 |
| 6 | 3 | 0.8 | <100 |

The color of the cocoyl chloride of all six batches (using recycled catalyst) is found to be colorless and identical in all respects. Non-catalyzed reaction which was run in parallel, under similar conditions, showed more than 10% of unconverted fatty acid after 8 hours. Continuing the reaction further did not reduce the unconverted fatty acid.

Example 13

Synthesis of lauroyl chloride from lauric acid Using oxalyl chloride and the Catalyst of Example 9

To a stirred molten mass of lauric acid (40 g, 200 mmol) and the polymeric catalyst (0.8 g) at 45° C. under nitrogen blanket, was added oxalyl chloride (28 g, 220.5 mmol) and the reaction was continued at 30-35° C. The progress of reaction was monitored by potentiometric titration that evaluates the unconverted lauric acid. The reaction went to completion after 2 hours with less than 1% by weight of unconverted lauric acid in the product.

Example 14

Synthesis of benzoyl chloride from benzoic acid Using the Catalyst of Example 9

To a stirred mixture of benzoic acid (36.6 g, 300 mmol) in dichloromethane (60 mL) and the polymeric catalyst of Example 9 (0.8 g) at 25 to 30° C. under nitrogen blanket, was added thionyl chloride (39 g, 327.7 mmol) over a period of 30 minutes. The progress of the reaction was monitored by potentiometric titration to determine the unconverted benzoic acid. In 3 hours the reaction was completed with less than 1% by weight of unconverted benzoic acid in the product. Filtration of the catalyst and removal of solvent furnished benzoyl chloride in quantitative yield.

Example 15

Synthesis of p-methoxy cinnamoyl chloride Using the Catalyst of Example 9

To a stirred mixture of p-methoxy cinnamic acid (26.7 g, 150 mmol) in dichloromethane (80 mL) and the polymeric catalyst of Example 9 (0.55 g) at 25 to 30° C. under nitrogen blanket, was added thionyl chloride (18.0 g, 151.3 mmol) over a period of 30 minutes. The progress of reaction was monitored by potentiometric titration to determine the unconverted acid. The reaction gets completed in 6 hours with less than 1% of p-methoxy cinnamic acid in the product. Filtration of catalyst and removal of solvent resulted in quantitative yield of p-methoxy cinnamoyl chloride.

Example 16

Synthesis of methoxy acetyl chloride Using the Catalyst of Example 9

To a stirred mixture of methoxy acetic acid (36 g, 400 mmol) and the polymeric catalyst of Example 9 (0.8 g) at 25 to 30° C. under nitrogen blanket, was added thionyl chloride (52.36 g, 440 mmol) over a period of 30 minutes. Progress of the reaction was monitored by the gas chromatographic analysis as well as by potentiometric titration to determine the unconverted methoxy acetic acid. In 3 hours the reaction was completed with less than 1% by weight of unconverted methoxy acetic acid in the product.

Example 17

Synthesis of cocoyl chloride Using the Catalyst of Example 11

To a stirred mixture of cocofatty acid (it is a mixture of C8 to C16 fatty acid with average molecular weight of 200, 40 g, 200 mmol) and 0.8 g of resin catalyst of Example 11 at room temperature under nitrogen atmosphere, thionyl chloride (25 g, 210 mmol) was added over a period of 30 minutes. The reaction was continued at 30-35° C. and the progress was monitored by estimating the unconverted fatty acid. The reaction was stopped after 4 hours when the free fatty acid was found to be less than 1.0%. The catalyst was filtered and recycled twice with same rate of catalysis. Unconverted coco fatty acid was found to be less than 1.0% by weight after 4 hours in the second and third cycle as well.

Example 18

Synthesis of pivaloyl chloride from pivalic acid Catalyzed by the polymer of Example 9

To a stirred molten mass of pivalic acid (41 g, 401 mmol) and the polymeric catalyst of Example 9 (0.8 g) at 45° C. under nitrogen blanket, was added oxalyl chloride (55.85 g, 440 mmol) and the progress of reaction was monitored by potentiometric titration that evaluates the unconverted pivalic acid. The reaction was completed after 3 hours with less than 1% by weight of unreacted pivalic acid in the product.

Example 19

Synthesis of octyl chloride from n-octanol Catalyzed by the Polymer of Example 9

To a stirred molten mass of n-octanol (52 g, 400 mmol) and the polymeric catalyst of Example 9 (1 g) at 25 to 40° C. under nitrogen blanket, was added thionyl chloride (52.5 g, 441 mmol). The temperature was raised to 70° C. and the reaction is continued. The progress of reaction was monitored by the gas chromatography. The reaction was found to be completed after 8 hours with less than 1% by weight of unconverted n-octyl alcohol in the product. Non catalyzed reaction ran in parallel, under similar conditions mainly resulted in dioctyl sulphonate (85%) with very little (15%) formation of octyl chloride even after 8 hours.

Example 20

Synthesis of behenyl chloride from behenyl alcohol Catalyzed by the Polymer of Example 9

To a stirred molten mass of behenyl alcohol (48 g, 150.5 mmol) and the polymeric catalyst of Example 9 (1.0 g) at 55 to 60° C. under nitrogen blanket, is added thionyl chloride (19.7 g, 165.5 mmol) and the reaction is continued at the same temperature. The progress of reaction is monitored by the gas chromatographic analysis using appropriate capillary column that separates fatty alcohols from the corresponding fatty alkyl chloride. The reaction was found to be complete after 8 hours with less than 1% by weight of unconverted behenyl alcohol in the product.

Example 21

Synthesis of undecylenoyl chloride by chlorination of undecylenic acid Using Catalyst of Example 9

To a stirred mixture of undecylenic acid (37 g, 200.8 mmol) and the polymeric catalyst of Example 9 (0.75 g) at room temperature under nitrogen atmosphere, oxalyl chloride (28 g, 220.5 mmol) is added over 30 minutes. The reaction is continued at 30-35° C. and the progress of the reaction is monitored by estimating the unconverted fatty acid. The reaction was stopped after 3 hours when the free undecylenic acid was found to be less than 1.0% by weight.

ADVANTAGES OF THE INVENTION

1) Organic acid chlorides and alkyl chlorides are industrial bulk chemicals and the steps that are required for clean isolation of catalyst from product result in huge losses of yield as well cost of disposal of waste that gets generated as part of purification. In view of the large volumes of these chemicals used by the industry, avoiding any loss in the yield of the desired product and avoiding any waste generation, will have serious positive impact on the environment as well as on the economics. Heterogeneous catalyst of the present invention (Compounds of Formula I) obviates need for isolation of products, the acid chlorides and alkyl chlorides by purification steps like distillation or crystallization.

2) The heterogeneous catalyst (Formula I) of this patent application is robust and can be recycled several times.

3) The heterogeneous catalyst (Formula I) of the present invention is based on functionalization of commercially available polystyrene in solid granular easy-to-filter form. The resin form of polystyrene catalyst in 20 to 500 mesh size is easy to isolate from the product, acid chloride and enables recycle of the catalyst.

4) The polystyrene catalyst is equally effective in chlorination of some of the organic acid substrates in solvents. The recyclability of this polystyrene backboned carboxamide catalyst of the present invention in solvents like commercially cheaper solvents such as dichloromethane or tetrahydrofuran (THF) is established.

5) The recyclable polystyrene based catalyst of the present invention catalyzes chlorination of a wide range of substrates (acids and alcohols) including, small or long chain aliphatic, unsaturated and aromatic substrates as well.

6) The resultant products of chlorination catalyzed by the polymeric catalyst of the present invention (Formula I) are clean and without any degradation products. In most cases the starting acids and alcohols are liquids or low melting solids and hence heterogeneous catalysis is done without any solvent. If needed, the chlorination can be effected very conveniently in a solvent like dichloromethane.

7) The heterogeneous catalyst of the present invention avoids using of toxic N, N-dimethyl formamide (DMF) type of catalysts (homogeneous catalysis) that are soluble in organic acid chlorides or alkyl chlorides.

8) Since the distillation/crystallization/phase separation steps (required to isolate dissolved catalyst from the product) are obviated during the manufacture of organic acid chlorides, there is no generation of waste (undistilled residue or concentrated mother liquors from crystallization) and hence in addition to the advantage of lesser energy consumption, a significant saving on the waste disposal is accomplished. This meets the principles of green chemistry (Anastas P. T. and Warner J. C., 1998) for the chlorination process. The chlorinated intermediates (acyl chlorides or alkyl chlorides) that are used in subsequent end products enable the whole process sequence of Green Chemistry. The commercially relevant example is the synthesis of fatty acid chloride that can be used without any purification for subsequent manufacture of surfactants on commercial scale (thousands of metric tonnes). This fatty acid chloride synthesis using recyclable polymeric catalyst of the present invention renders the process of surfactant manufacture (N-acyl glycinates, N-acyl sarcosinates, N-acyl glutamates etc) as green, eco-friendly and sustainable. It is truly 'Green Chemistry' as both the product and the process do not use or generate any hazardous chemicals.

9) It is also easily understood by those skilled in the art that the resinous catalyst of the present invention can be immobilized and thus fixed bed obtained can be used for continuous manufacture of chlorination of organic acids and alcohols.

We claim:
1. A polymer catalyst having a group of Formula Ia tethered to a polystyrene backbone,

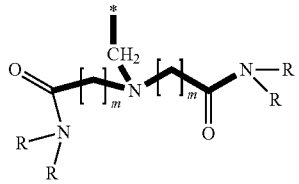

Formula Ia wherein:
R is selected from the group consisting of $C_1$ to $C_5$ alkyl groups;
'm' has a value ranging from 1 to 5; and
* marks a point of attachment to a para-position of a styrene moiety in the polystyrene backbone.

2. The polymer catalyst according to claim 1, wherein the polystyrene backbone is derived from either chloromethyl polystyrene or aminomethyl polystyrene in resin form.

3. A process for chlorination of an organic acid or an organic alcohol, comprising:
reacting the organic acid or the organic alcohol with a chlorinating agent in the presence of the polymer catalyst of claim 1,
wherein the polymer catalyst is used as a catalyst;
wherein the chlorinating reagent is selected from the group consisting of carbonyl chloride, thionyl chloride or oxalyl chloride.

4. A process for preparation of a polymer catalyst, comprising
a) reacting an acrylate or an iminodiester with a functionalized polystyrene to obtain an amino diester unit tethered to a polystyrene backbone; and
b) subjecting the amino diester unit tethered to the polystyrene backbone to aminolysis with a secondary or cyclic amine to obtain the polymer catalyst,

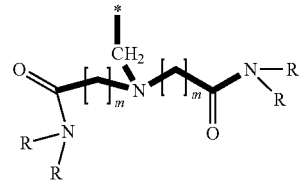

Formula Ia wherein the polymer catalyst has a group of Formula Ia tethered to the polystyrene backbone, where R is selected from the group consisting of $C_1$ to $C_5$ alkyl groups; 'm' has a value ranging from 1 to 5; and * marks a point of attachment to a para-position of a styrene moiety in the polystyrene backbone.

5. The process according to claim 4, wherein the functionalized polystyrene is chloromethyl polystyrene having a chloromethyl label content ranging from 0.5 mmol/g to 5 mmol/g of resin.

6. The process according to claim 4, wherein the functionalized polystyrene is aminomethyl polystyrene having an amino label content of about 2 mmol/g of resin.

7. The process according to claim 4, wherein the functionalized polystyrene is chloromethyl polystyrene; and step (a) comprises reacting the chloromethyl polystyrene with an iminodiester.

8. The process according to claim 4, wherein the functionalized polystyrene is aminomethyl polystyrene; and step (a) comprises reacting the aminomethyl polystyrene with an acrylate ester.

* * * * *